United States Patent [19]

Siarkiewicz et al.

[11] 4,304,242
[45] Dec. 8, 1981

[54] PHOTOSTIMULATOR

[75] Inventors: Piotr H. Siarkiewicz; Bogdan W. Zacharski, both of Warsaw, Poland

[73] Assignee: Instytut Psychoneurologiczny, Warsaw, Poland

[21] Appl. No.: 54,367

[22] Filed: Jul. 3, 1979

[30] Foreign Application Priority Data

Jul. 12, 1978 [PL] Poland .................................. 208376

[51] Int. Cl.³ .............................................. A61B 5/00
[52] U.S. Cl. .................................................... 128/745
[58] Field of Search ................................. 128/731, 745

[56] References Cited

U.S. PATENT DOCUMENTS 3,288,546 11/1966 Gans .................................... 128/745

FOREIGN PATENT DOCUMENTS 2507723 8/1976 Fed. Rep. of Germany ...... 128/745

OTHER PUBLICATIONS

Troelstra et al., "IEEE Transactions on Biomedical Engineering", vol. 22, No. 5, pp. 369-378, Sep. 1979.

Primary Examiner—William E. Kamm
Attorney, Agent, or Firm—Ladas & Parry

[57] ABSTRACT

An electrophysiological photostimulator, particularly to study evoked visual potentials, comprises a luminescent matrix source, its surface having unit sources arranged in order under a control unit. The control photostimulator in the control unit has function, shape and form programmers, which control the stimulation source that is the luminescence matrix through an adder with a steady luminance level unit and a system for switching over the y and y lines and lighting up systems. The shape and form programmers solve the problem of dynamic stimuli understood as successive alternations of shape during one stimulus T. The described photostimulator facilitates the examinations in the field of electroencephalography, electroretinography, electronstagmography and electroocculography. Owing to the application of the other kinds of stimuli instead of the light ones the described photostimulator can successively be used in an other branches of electrophysiology, where a collective stimulation of the respective physiological organs is necessary.

1 Claim, 4 Drawing Figures

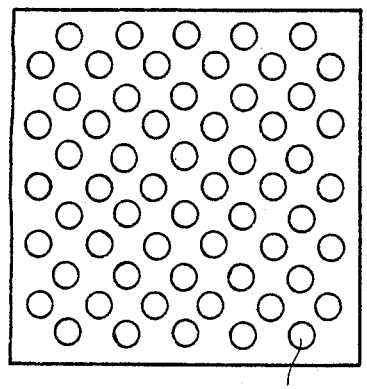
Fig. 2 LIGHT EMITTING ELEMENT
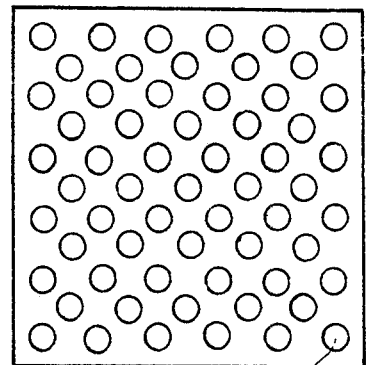
Fig. 3 LIGHT EMITTING ELEMENT
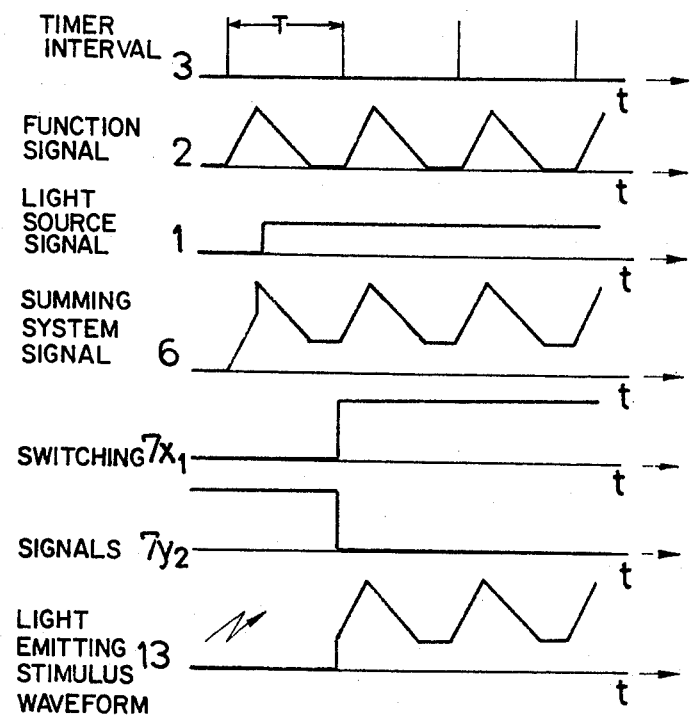
Fig. 4

PHOTOSTIMULATOR

BACKGROUND OF THE INVENTION

This invention relates to a photostimulator to be used for electrophysiological examinations, and particularly for the measurements of evoked visual potentials, suited to cooperation with automatic systems for analysis of electrophysiological signals, the said photostimulator consisting of a stimulation source of a biological object and a control unit for the control of the said source.

Those skilled in art know the following designs of photostimulators producing light stimuli (collective work edited by John E. Desmedt entitled "Visual evoked potentials in man: new developments"—Clarendom Press—Oxford—1977—page 3—15). Electronic photostimulators with spark lamps with pulse-like operation do not provide any possibility of application of a function understood as a variability of a light flux of an individual glowing element (all glowing elements emit the same flux in the form of arbitrary variations e.g. sinudoidal, trapezoid etc. with a constant component of the light flux or without it), the shape being understood as a steady configuration of glowing elements on a luminescence matrix for a given time interval (only some of the glowing elements on the luminescence matrix are simultaneously glowing, said glowing elements forming e.g. horizontal or vertical stripes, grates, bents, circles, letters or the like, or, finally, the chosen fields such as e.g.: horizontal or vertical halves, quarters etc.), the shape being dependent upon the reflection screen being used on which black and white fields are painted (check or the so called checkered pattern), imitating the glowing elements at the time of illumination of the screen by the spark lamp. Electronic photostimulators with spark lamps also do not afford any possibility of varying the form understood as a continuous or step-like displacement of the shape on a luminescence matrix (reversibility of the neighbouring glowing elements, or the whole patterns, that is stripes, hemispheres, quarters, as well as circulation of the stripes or quarters around a central point). Electronic photostimulators with a TV kinescope are known on which an arbitrary shape can be obtained, but with the limited possibilities of reproduction of a function or form because of the extinguishing time (after-glow duration) of a kinescope screen. Optical photostimulators with mechanical projecting systems and film screens, where the required function, shape and form can be obtained by means of the respective motion of diaphragms and mirrors are known, but with considerable time limitations of the said function, shape and form depending upon inertia of the mechanical systems (diaphragms and mirrors). Those skilled in art also know the photostimulator described in the Polish patent specification No. 73,416, which may be put in a group of electronic photostimulators with a spark lamp and with pulse-like operation. This invention the design of such a photostimulator which would render possible widening of the range of possible examinations of eyesight in connection with cortex reactions (evoked visual potentials) to light stimuli.

SUMMARY OF THE INVENTION

The essence of the invention consists in that the said photostimulator includes a stimulation source and a control unit for the control of the said source. The stimulation source is produced by the surface of a luminescence matrix on which unit stimulation sources (glowing elements) are arranged, controlled by a system for switching over sets of lines x and y and by systems for starting up the glowing elements. Unit stimulation sources are arranged on a spacial cylindrical, spherical or paraboidal surface or the segments thereof. Apart from this, the glowing points are arranged over this surface in an orderly way, that is linearly, radially, spirally, circularly, in a rosette-like pattern, or forming arbitrary alphabet signs or ciphers. A control unit for the control of the stimulation source consists of a time interval generator with two outputs, the frequency of the first output, being a multiple of the selected time interval frequency of the second output and of a function programmer, a wave shape programmer and a wave form progrmmer. The above mentioned wave shape programmer and wave form programmer circuits are controlled in parallel by the time interval generator, whereas the wave shape programmer circuit is controlled by the first timer output with the multiple frequency of the time intervals and by the wave form programmer, system for switching over the x and y axes programmed directly by the wave shape programmer circuit.

The function, shape and form of the light stimuli renders possible separation of reactions of the respective units of photosensors on the retina of the subject to statical stimuli, understood as stimuli consisting of one shape and the dynamic stimuli understood as the successive alterations of shape during one stimulus. Moreover, the above mentioned stimuli facilitate the examination in electroencephalography, electroretinography, electronstagmography and electrooculography.

Owing to the application of the other kinds of stimuli not necessarily the visual ones, this stimulator can be successfully used in all other branches of electrophysiology, which require a group stimulation of the physiological organs.

BRIEF DESCRIPTION OF THE DRAWINGS

In the accompanying drawing,

FIG. 2 is a schematic representation on a highly-magnified scale of a segment of the curved (not shown) surface of the luminescent matrix in the n-th time interval, FIG. 3 is the corresponding segment of the matrix in the (n+1) time interval, FIGS. 2 and 3 being examples of reversibility of the adjacent glowing elements in the matrix, FIG. 4—illustrates several wave form control signals in the photostimulator circuitry for the control of the individual units in time and, particularly, light control signals for one of the glowing elements at the convergence of lines x1 and y2 visible in FIG. 1.

DESCRIPTION OF THE PREFERRED EMBODIMENT

Figure 1:
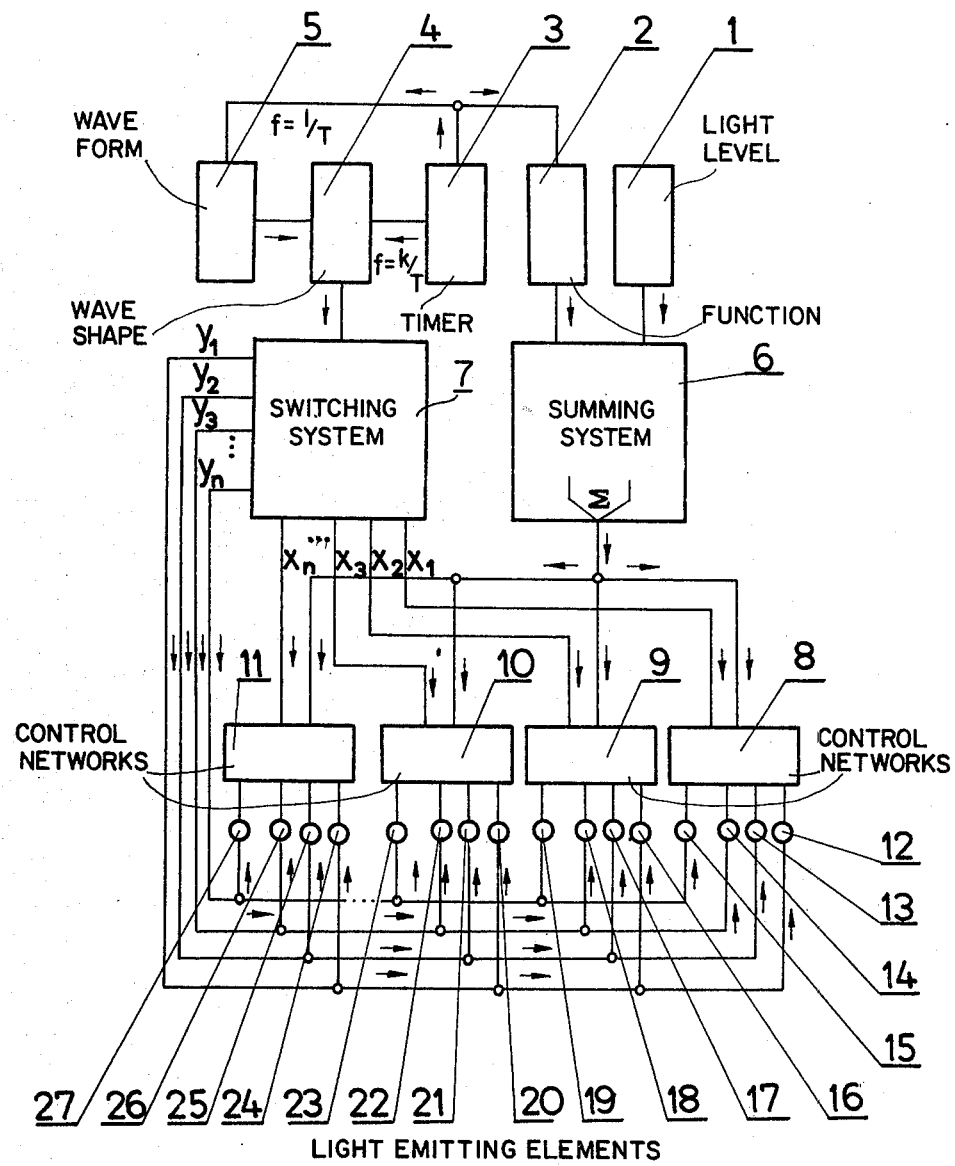
FIG. 1 is block diagram of the stimulator.

A photostimulator according to the invention consists of a control unit, including system 1 for a varying continuously the level of luminescence, a function programmer system 2, the time interval generator system 3, a signal wave circuit shape programmer 4, a signal wave circuit form programmer 5, a summing circuit 6 and a stimulation source (luminescence matrix), including system 7 for switching signals to "n" sets of x and y lines, the x lines being connected to control networks 8, 9, 10 and 11 for lighting up selected glowing elements, and the y lines being connected to the glowing elements 12, 13, 14, 15, 16, 17, 18, 19, 20, 21, 22, 23, 24, 25, 26 and 27.

The operation of the stimulator shown in FIG. 1 will now be described. The time interval generator system 3 operates as a clock generator with time period T, provided with two synchronous outputs, the signal frequency of one of these outputs being a multiple k of the signal frequency of the second output. The signal of period T is shown in the waveform marked 3 in FIG. 4. It will be seen that each waveform of FIG. 4 has the same reference numeral as the circuit unit which generates it. The function programmer system 2 generates an individual pulse of the required function such as a trapezoid shaped wave form having pre-set parameters such as pulse duration, pulse rise time, pulse fall time (see waveform 2 of FIG. 4) after each pulse conveyed from system 3 with time period T. The pulse of the required function is added in summing circuit 6 to the valve of the constant component from system 1 (wave form 1) for varying the steady state level of luminescence. The signal (waveform 6) thus added passes to the networks 8, 9, 10, 11 for lighting up the glowing elements 12, 13, 14, 15, 16, 17, 18, 19, 20, 21, 22, 23, 24, 25, 26 and 27. Wave form programmer circuit 5 activated by the pulse of the function system 3 transmits a signal to wave shape circuit 4 providing a control signal with a displacement of the desired shape on the luminescence matrix after each stimulus of the time period T. Wave shape programmer circuit 4 transmits this signal to the system 7 for switching over the selected x and y lines, which causes transmission of pulses along the x lines (waveform $7x_1$) to the networks 8, 9, 10 and 11 for lighting up the glowing elements and along the y lines (waveform $7y_2$) to the respective glowing elements 12, 13, 14, 15, 16, 17, 18, 19, 20, 21, 22, 23, 24, 25, 26 and 27. The waveform 13 of FIG. 4 shows the flux emitted by light-emitting element 13/glowing element 13 in response to waveform $7x_1$ and $7y_2$. FIGS. 2 and 3 show an example of reversibility of the adjacent glowing elements in a matrix segment for the static stimuli. In order to obtain a dynamic stimulus it is necessary to excite the signal wave shape programmer circuit 4 with the corresponding number n of pulses from the timer system 3 as obtained from the time interval generator, the frequency of the said pulses being k-times greater than frequency 1/T of the pulses for activating function system 2 and wave form circuit 5. In such a case the variation in the shape on the luminescence matrix will be effected at time intervals k-times shorter than the duration of the stimulus of period T. The dynamic stimuli are distinguishable, when the relationship given below is fulfilled:

$$T > n(T/K) \text{ such that } k > n.$$

We claim:

1. A photostimulator adapted for use in electrophysiological examinations of subjects by utilizing evoked visual potential signals, comprising a stimulation source of signals and a control apparatus for said signal source wherein said control apparatus includes a time interval generator system, connected for generating two output signals, the pulse frequency of one such output signal being a multiple "k" of the pulse frequency of the second output signal, a function programmer system responsive to said second output signals from said timer system, a signal wave form programmer circuit connected to be activated by said second output signal from said timer system, a control signal wave shape programmer circuit having two input sources, one of which is connected to the output of said wave form programmer circuit and the other of which is connected to be responsive to said first output signal from said generator system said stimulation source further including a segment of a curved surface in the form of a luminescent matrix in which there are arranged a preselected pattern of closely adjacent light emitting elements, a system of control networks connected for supplying light generating signals to said elements in response to a pair of signals directed to said networks, a summing circuit responsive to said source of stimulation signals and to output signals from said function programmer system to provide a first set of control signals to said networks, and a switching system responsive to said wave shape programmer circuit for generating a pair of output switching signals, corresponding sets of x and y lines, any two of which comprise an address for a corresponding one of said light emitting elements, and connected for transmission of said output switching signals along selected ones of said y lines directly to said elements and along selected ones of said x lines to said control networks.

* * * * *